(12) United States Patent
Marchewitz

(10) Patent No.: US 8,084,446 B2
(45) Date of Patent: Dec. 27, 2011

(54) USE OF DHEA DERIVATIVES FOR ENHANCING PHYSICAL PERFORMANCE

(76) Inventor: Eric Marchewitz, Las Vegas, NV (US)

( * ) Notice: Subject to any disclaimer, the term of this patent is extended or adjusted under 35 U.S.C. 154(b) by 1202 days.

(21) Appl. No.: 11/411,530

(22) Filed: Apr. 26, 2006

(65) Prior Publication Data

US 2006/0241093 A1 Oct. 26, 2006

Related U.S. Application Data

(60) Provisional application No. 60/762,328, filed on Jan. 26, 2006, provisional application No. 60/694,813, filed on Jun. 29, 2005, provisional application No. 60/674,525, filed on Apr. 26, 2005.

(51) Int. Cl.
    *A61K 31/56* (2006.01)
(52) U.S. Cl. .................................................. 514/182
(58) Field of Classification Search ............... 514/171, 514/182
    See application file for complete search history.

(56) References Cited

U.S. PATENT DOCUMENTS

| | | | |
|---|---|---|---|
| 3,501,504 A | 3/1970 | Klimstra | |
| 4,587,235 A | 5/1986 | Bittler et al. | |
| 4,634,694 A | 1/1987 | Loozen et al. | |
| 5,028,631 A | 7/1991 | Schwartz et al. | |
| 5,079,377 A | 1/1992 | Yoshihama et al. | |
| 5,424,463 A | 6/1995 | Lardy et al. | |
| 5,521,167 A | 5/1996 | Gobbini et al. | |
| 5,585,371 A | 12/1996 | Lardy | |
| 5,744,462 A | 4/1998 | Schwartz et al. | |
| 5,776,923 A | 7/1998 | Labrie | |
| 5,804,576 A | 9/1998 | Schwartz et al. | |
| 5,948,434 A | 9/1999 | Labrie | |
| 6,153,606 A | 11/2000 | Lardy et al. | |
| 6,368,617 B1 | 4/2002 | Hastings et al. | |
| 6,489,313 B1 | 12/2002 | Lardy et al. | |
| 6,586,417 B1 | 7/2003 | Abraham | |
| 6,667,299 B1 * | 12/2003 | Ahlem et al. | 514/178 |
| 6,794,374 B1 | 9/2004 | Weeks | |
| 6,924,274 B2 | 8/2005 | Lardy et al. | |
| 6,964,954 B2 | 11/2005 | Dalko et al. | |
| 7,002,028 B2 | 2/2006 | White et al. | |
| 2004/0001817 A1 | 1/2004 | Giampapa | |

OTHER PUBLICATIONS

Brose et al., Journal of Gerontology, 2003;58(1):11-19.*
Simpson et al., AIDS, 1004;18:1403-1412.*
Correspondence from J. McCormack to E. Marchewitz, sent on Jul. 7, 2011, regarding U.S. Appl. No. 11/411,530.
Klimstra et al., "The Synthesis of 3β-Hydroxyestr-4-en-17-one and 3β-Hydroxyandrost-4-en-17-one," *Steroids* 10(4):411-424 (1967).
Rosenberg, "Synthesen in der Reihe der Sexualhormone," Eidgenossischen Technical University in Zurich (1936).

* cited by examiner

*Primary Examiner* — San-Ming Hui

(57) ABSTRACT

A method is disclosed for administering a DHEA derivative or a physiologically acceptable salt, ester or ether thereof for one of decreasing body weight, reducing adipose tissue, increasing endurance, as an anti-aging compound and generating production of red blood cells.

4 Claims, No Drawings

USE OF DHEA DERIVATIVES FOR
ENHANCING PHYSICAL PERFORMANCE

RELATED APPLICATIONS

This application claims priority benefit of U.S. provisional patent applications No. 60/674,525, filed on Apr. 26, 2005, No. 60/694,813 filed Jun. 29, 2005, and No. 60/762,328 filed Jan. 26, 2006.

FIELD OF THE INVENTION

This invention relates to use of derivatives of dehydroepiandrosterone (3-beta-hydroxy-5-androst-1-en-17-one or simply "DHEA") to enhance physical performance, and more particularly to the use of DHEA derivatives for anti-aging benefits, decreasing body weight, reducing adipose tissue, and increasing endurance.

BACKGROUND OF THE INVENTION

The adrenal gland produces many steroid hormones. These steroid hormones play a major role in many body processes including, for example, skeletal muscle growth, red blood cell production (erythropoiesis), regulation of glucose and insulin levels and cellular aging. The steroids produced by the adrenal gland can be divided into three groups: glucocorticoids, which influence carbohydrate metabolism; mineralocorticoids, which control electrolyte and water balance; and sex steroid hormones. Glucocorticoids such as cortisol regulate catabolism of skeletal muscle proteins into amino acids. These amino acids are then transported to the liver and converted into glucose during gluconeogenesis. Excessive amounts of glucocorticoids can result in higher blood glucose and insulin levels and can contribute to increased body fat and type II diabetes. Glucocorticoids are also known to play a role in the aging process by increasing cellular and mitochondrial breakdown.

The second group of adrenal steroids, the mineralocorticoids such as aldosterone help the body to retain sodium and water. Excesses of mineralocorticoids can result in hypertension and cardiovascular disease.

The third group of adrenal steroids include androgens and DHEA. Adrenal androgens oppose the actions of glucocorticoids and result in skeletal muscle anabolism (the opposite action of catabolism), reductions in blood glucose and insulin levels, reduction in body fat, and are believed to decrease the rate of cellular aging and increased red blood cell production. DHEA production by the adrenal glands is known to decline markedly as aging progresses.

With normal younger adults, all three groups of adrenal steroids are produced in a healthy balance. However, as people age, less DHEA is produced resulting in relatively greater amounts of glucocorticoids and mineralocorticoids and disruption of this balance.

DHEA supplementation is believed be useful in treatment of aging and obesity and to stimulate erythropoiesis and skeletal muscle anabolism. In addition, supplemental DHEA can help restore the balance of adrenal steroids.

DHEA is commonly used as a dietary supplement. Unfortunately, DHEA is rapidly metabolized by liver enzymes referred to as sulfotransferases. Sulfotransferases rapidly convert the much of the supplementary DHEA into DHEA sulfate, which is quickly excreted from the body and is not effective as an anti-aging, muscle-building or fat reduction compound. In addition, DHEA sulfate does not restore the balance of the adrenal steroids discussed above. As a result, frequent and larger doses of DHEA must be taken.

DHEA is also metabolized in the body to one of several compounds including, for example, etiocholanolone (5-beta-androstan-3-alpha-ol-17-one), beta etiocholanolone (5-beta-androstan-3-beta-ol-17-one), androsterone (5-alpha-androstan-3-alpha-ol-17-one), epiandrosterone (5-alpha-androstan-3-beta-ol-17-one), 7-keto-DHEA, 7-alpha-hydroxy-DHEA, 7-beta-hydroxy-DHEA, androstenedione, estrone and estradiol.

There is great individual variability in the metabolism of oral DHEA. The DHEA metabolites estrone and estradiol can result in negative estrogenic side effects for males including growth of male breast tissue, known as gynecomastia. Some individuals have poor bioavailability of DHEA as a result of sulfation in the liver, and large doses must be taken to elicit any desired effects. These increased doses of DHEA can result in increased conversion to estrone and estradiol, with resulting negative side effects.

It would be desirable to provide compounds which can be used to help provide the beneficial effects of high DHEA levels in the body for extended periods of time, yet reduce the undesired DHEA side effects discussed above.

SUMMARY OF THE INVENTION

In accordance with a first aspect, a method is disclosed for administering a DHEA derivative or a physiologically acceptable salt, ester or ether thereof for decreasing body weight, reducing adipose tissue, increasing endurance, as an anti-aging compound and/or increasing production of red blood cells.

From the foregoing disclosure and the following more detailed description of various preferred embodiments it will be apparent to those skilled in the art that the present invention provides a significant advance in the methods of administering anti-aging compounds, for decreasing body weight and reducing adipose tissue, and increasing endurance. Additional features and advantages of various preferred embodiments will be better understood in view of the detailed description provided below.

DETAILED DESCRIPTION OF CERTAIN
PREFERRED EMBODIMENTS

It will be apparent to those skilled in the art, that is, to those who have knowledge or experience in this area of technology that many variations are possible for the method of administering DHEA derivatives for enhancing physical performance. The following detailed discussion of various alternative and preferred features and embodiments will illustrate the general principles of the invention with reference to improved methods of enhancing physical performance by administering DHEA derivatives as orally available dietary supplements. Other embodiments suitable for other applications will be apparent to those skilled in the art given the benefit of this disclosure.

As used herein, a derivative of a compound refers to a species having a chemical structure that is similar to the compound, yet containing a chemical group not present in the compound and/or deficient of a chemical group that is present in the compound. The substance to which the derivative is compared is known as the "parent" substance. Here, for example, the parent compound is the androstane steroid DHEA. A derivative may be made by modification of the parent compound or by synthesis from other starting materials that are not similar to the parent.

DHEA derivatives disclosed herein are advantageous in that they last longer in the body and are resistant to conversion to estradiol and estrogen, thereby advantageously providing the benefits of supplemental DHEA (including anti-aging benefits, decreased body weight, reduction of adipose tissue, increased endurance and/or increasing production of red blood cells) while reducing the negative side effects. Long-lasting DHEA derivatives are of the general formulas shown below, starting with the androst-1ens:

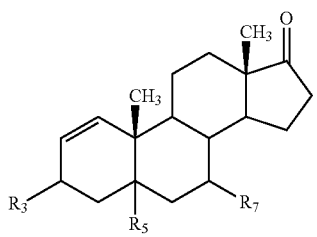

wherein R3 is one of α-OH, β-OH, R5 is one of αH and βH, and R7 is one of H and $CH_3$. DHEA derivatives made according to the above formula can consist of 3-alpha-hydroxy-5-alpha-androst-1-en-17-one, 3-beta-hydroxy-5-alpha-androst-1-en-17-one, 3-alpha-hydroxy-5-alpha-7-alpha-methyl-androst-1-en-17-one, 3-beta-hydroxy-5-alpha-7-alpha-methyl-androst-1-en-17-one, 3-alpha-hydroxy-5-beta-androst-1-en-17-one, 3-beta-hydroxy-5-beta-androst-1-en-17-one, 3-alpha-hydroxy-5-beta-7-alpha-methyl-androst-1-en-17-one, and 3-beta-hydroxy-5-beta-7-alpha-methyl-androst-1-en-17-one, along with any salts, esters or ethers thereof.

Long lasting DHEA derivatives also include the following androst-4-ens:

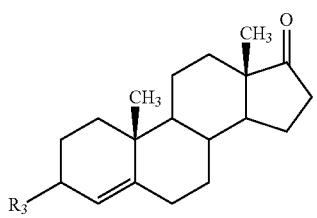

wherein R3=one of is α-OH, β-OH. DHEA derivatives made according to the above formula can consist of 3-beta-hydroxy-androst-4-en-17-one and 3-alpha-hydroxy-androst-4-en-17-one along with any salts, esters or ethers thereof.

Long lasting DHEA derivatives also include the androst-5-en compound: 3-beta-hydroxy-7-alpha-methyl-androst-5-en-17-one, or any salts, esters or ethers thereof, reproduced immediately below:

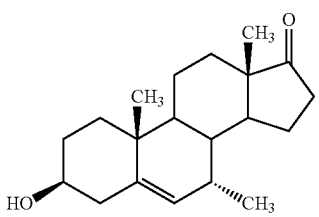

Long lasting DHEA derivatives also include the androstan compound, 3-alpha-hydroxy-5-alpha-androstan-7,17-dione, or any salts, esters or ethers thereof, reproduced immediately below:

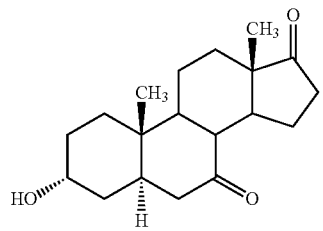

Long lasting DHEA derivatives also include 19-norandrost-4-en compounds according to the general formula:

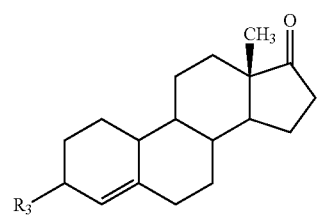

wherein R3=one of is α-OH, β-OH. DHEA derivatives made according to the above formula can consist of 3-beta-hydroxy-norandrost-4-en-17-one and 3-alpha-hydroxy-norandrost-4-en-17-one or any salts, esters or ethers thereof.

Long lasting DHEA derivatives also include 19-norandrost-5-en compounds according to the general formula:

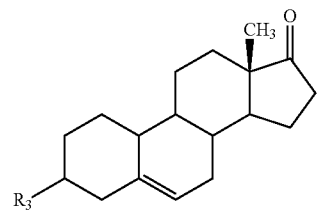

wherein R3=one of is α-OH, β-OH. DHEA derivatives made according to the above formula can consist of 3-beta-hydroxy-norandrost-5-en-17-one and 3-alpha-hydroxy-norandrost-5-en-17-one or any salts, esters or ethers thereof.

In accordance with conventional steroid carbon numbering, an atom or functional group attached to a ring depicted herein is termed α (alpha) if it lies below the plane of the paper or β (beta) if it lies above the plane of the paper. When R3 and/or R7 have one functional group listed, it is understood that the fourth bond to the carbon is hydrogen. Other related DHEA derivatives suitable for administering anti-aging compounds, for decreasing body weight and reducing adipose tissue, for increasing production of red blood cells and/or increasing endurance will be readily apparent to those skilled in the art, given the benefit of this disclosure.

All of the naturally occurring DHEA derivative compounds disclosed herein would preferably be administered orally mixed with solid or liquid carriers in appropriate unit doses.

The preferred amount of the active ingredient that is to be administered, would depend on various factors such as the age and weight of the user. An effective oral daily dosage of the described DHEA derivatives can comprise 50-2000 mg daily, and most preferably about 100-800 mg daily. A preferred embodiment might be to administer the oral dose as a soft gelatin capsule or oral liquid suspension, either in two to three divided doses per day (i.e., 50 to 400 mg twice per day, or 25 mg to 200 mg four times per day). The DHEA derivatives as disclosed herein may also be administered transdermally using acceptable liquid vehicles, sublingually, transrectally (by suppository) intranasally, intravenously, subcutaneously, or by intramuscular injection. The DHEA derivatives as disclosed herein may also be mixed with dietary supplements such as creatine if desired.

Example 1

Capsules. 1 kg of the DHEA derivative, 3-beta-hydroxy-norandrost-4-en-17-one is mixed with microcrystalline cellulose, and placed into 10,000 hard-gelatin capsules. Each capsule contains 100 mg of 3-beta-hydroxy-norandrost-4-en-17-one.

Example 2

Capsules. 1 kg of the DHEA derivative 3-beta-hydroxy-norandrost-5-en-17-one is mixed with 5 kg of creatine and placed into 10,000 hard-gelatin capsules. Each capsule contains 100 mg of 3-beta-hydroxy-norandrost-5-en-17-one and 500 mg creatine.

From the foregoing disclosure and detailed description of certain preferred embodiments, it will be apparent that various modifications, additions and other alternative embodiments are possible without departing from the true scope and spirit of the invention. The embodiments discussed were chosen and described to provide the best illustration of the principles of the invention and its practical application to thereby enable one of ordinary skill in the art to use the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of administering a DHEA derivative or a physiologically acceptable salt, ester or ether thereof as a compound that provides at least one or anti-aging adrenal hormonal balance, decreased body weight, reduction of adipose tissue, increased endurance, skeletal muscle growth, and increased production of red blood cells, of the general formula:

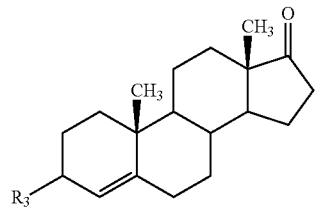

wherein R3 is one of α-OH and β-OH, wherein the DHEA derivative is administered orally.

2. The method of claim 1 wherein the DHEA derivative is administered in the form of a gel capsule.

3. The method of claim 1 further comprising administering the DHEA derivative with creatine.

4. A method of administering a DHEA derivative or a physiologically acceptable salt, ester or ether thereof as a compound that provides at least one of anti-aging adrenal hormonal balance, decreased body weight, reduction of adipose tissue, increased endurance, skeletal muscle growth, and increased production of red blood cells, of the general formula:

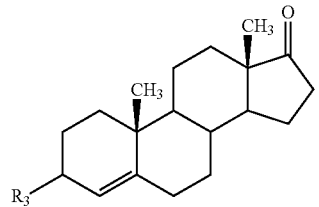

wherein R3 is one of α-OH and β-OH, and further comprising administering the DHEA derivative with creatine.

* * * * *